United States Patent [19]

Fling

[11] E Re. 28,560

[45] Reissued Sept. 30, 1975

[54] DIAPHRAGM EAR VALVE

[75] Inventor: John J. Fling, Malibu, Calif.

[73] Assignee: Sigma Engineering Company, North Hollywood, Calif.

[22] Filed: Nov. 7, 1973

[21] Appl. No.: 413,498

Related U.S. Patent Documents

Reissue of:

[64] Patent No.: 3,730,181
Issued: May 1, 1973
Appl. No.: 122,856
Filed: Mar. 10, 1971

U.S. Applications:

[63] Continuation-in-part of Ser. No. 858,600, Sept. 17, 1969, abandoned.

[52] U.S. Cl. ..... 128/152
[51] Int. Cl.[2] ..... A61F 11/02
[58] Field of Search ..... 128/152, 151, 145.5, 145.8; 181/33, 23; 137/517, 512.4, 512.5, 525

[56] References Cited

UNITED STATES PATENTS

| | | | |
|---|---|---|---|
| 2,465,606 | 3/1949 | Reynolds | 128/152 |
| 2,476,224 | 7/1949 | Rosenblatt | 128/152 |
| 2,487,038 | 11/1949 | Baum | 128/152 |
| 2,619,960 | 12/1952 | Reynolds | 128/152 |
| 3,084,707 | 4/1963 | Frye | 137/512.4 X |
| 3,335,671 | 8/1967 | Schoenecker et al. | 137/525 X |

FOREIGN PATENTS OR APPLICATIONS

| | | | |
|---|---|---|---|
| 385,082 | 12/1932 | United Kingdom | 128/152 |

*Primary Examiner*—Richard A. Gaudet
*Assistant Examiner*—Henry J. Recla
*Attorney, Agent, or Firm*—Huebner & Worrel

[57] ABSTRACT

A diaphragm ear valve for protection of the ear drum from the injurious percussive and repercussive overpressures of strong sound waves.

The ear valve or sound transmitter comprises a flexible diaphragm means which has a sound passage aperture therethrough. The diaphragm means is stretched radially outwardly and held by two catcher plate means each having a sound passage therethrough and annular holding means to retain the outer annular diaphragm bead. The apertures affording a sound path of sinuous configuration.

The ear valve is adapted to receive an ear canal fitting.

18 Claims, 10 Drawing Figures

INVENTOR.
JOHN J. FLING
By Huebner & Worrel
ATTORNEYS.

INVENTOR.
JOHN J. FLING
By Huebner & Worrel
ATTORNEYS.

DIAPHRAGM EAR VALVE

Matter enclosed in heavy brackets [ ] appears in the original patent but forms no part of this reissue specification; matter printed in italics indicates the additions made by reissue.

---

This application is a continuation-in-part of my pending U.S. Pat. application Ser. No. 858,600, filed Sept. 17, 1969 now abandoned.

BACKGROUND OF THE INVENTION

Potential ear damage is one of the problems man has been forced to endure in order to live in today's technologically advanced society. Jet planes, various manufacturing processes, and popular music are but a few of the numerous sources of loud and potentially damaging sounds which man's ears cannot constantly endure without suffering a decrease in sensitivity to high and low frequency sounds and eventual total loss of hearing.

Various attempts have been made to deal with this problem, such as attenuation devices having sliding valves, spring actuated closure means and diaphragm ear plugs. None of the prior art gives sufficient attenuation protection from high decibel sounds without sacrificing low and sound level efficiency.

SUMMARY OF THE INVENTION

The diaphragm ear valve of this invention is adapted to be used in conjunction with an ear canal fitting to form an assembly for insertion into the human ear canal, more particularly, the external auditory meatus of the ear.

The diaphragm ear valve operates so as to allow normal sounds, or sounds below a predetermined decibel level, to pass therethrough and into the inner ear, while at the same time preventing the passage of abnormally loud *sound and excessive changes of sound level* and therefore injurous sounds into the ear.

This invention is designed to attenuate ear damage from both percussive and repercussive sound wave pressure.

The invention includes a diaphragm, the material thickness of which may be varied to control the shut-off threshold, i.e., the decibel level, at which the valve will close.

The invention is designed so that an extremely sensitive diaphragm can be used thereby giving the valve a low decibel shutoff threshold.

The diaphragm of the invention may be extremely thin, and thus the valve will have a very fast speed of response to sudden decibel increases.

Further, means are provided on the diaphragm and a retaining member to radially stretch the diaphragm to facilitate the return of the diaphragm to its normal at rest position.

These and other *objects and* advantages *inherent in the diaphragm ear valve of the present invention* will become apparent from the following description and drawings wherein:

DETAILED DESCRIPTION OF THE PREFERRED EMBODIMENTS

Figure 1:
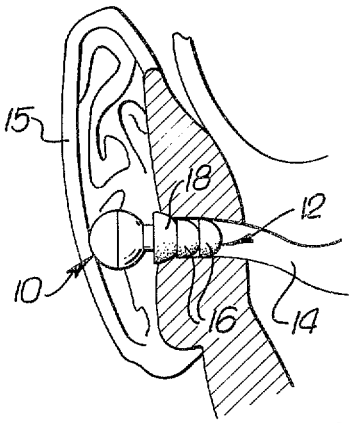
FIG. 1 is an environmental view of the diaphragm ear valve inserted into an ear canal fitting, and the entire assembly being fitted into the external auditory meatus of a human ear.

In FIG. 1 there is illustrated the diaphragm ear valve of the invention, generally designated 10, shown connected to a resilient ear canal fitting generally designated 12 which is inserted into the external auditory meatus 14 of a human ear 15.

Any type of ear canal fitting 12 may be utilized to seat in the canal 14. However, it is preferred that the fitting 12 be formed with a plurality of forward annular flanges 16 which bear against the external auditory meatus 14 to form a soundproof seal therebetween and a rear annular flange 18. Rear annular flange 18 is preferably larger in diameter than forward flanges 16 and the external auditory meatus 14 and limits the insertion of fitting 12 into the ear. No claim is made regarding the novelty of the ear canal fitting, which is a type well known in the art, but necessary for correct operation of the ear valve 10.

Figure 2:
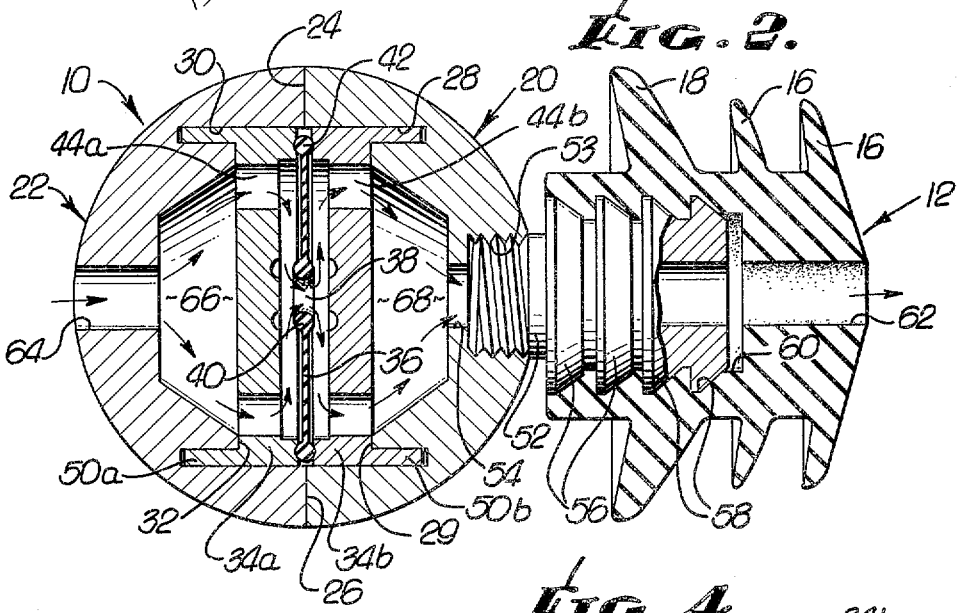
FIG. 2 is an enlarged cross-sectional view of the assembly illustrated in FIG. 1.
Figure 4:
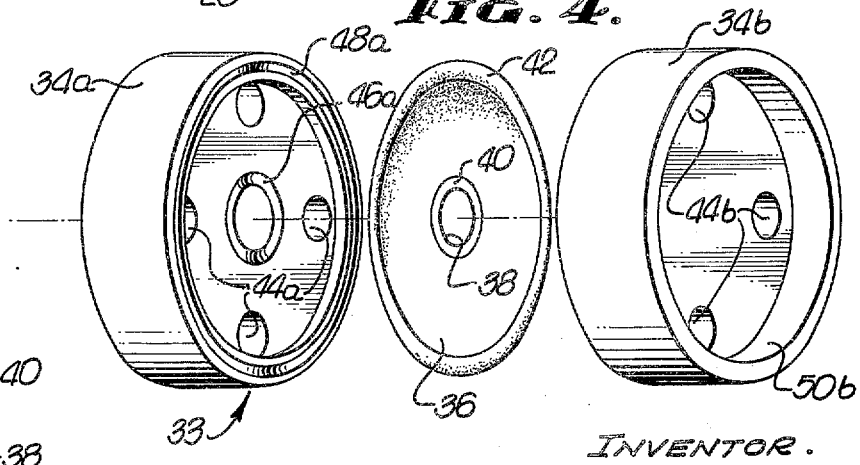
FIG. 4 is an exploded view of the portions of the ear valve shown in FIG. 3.

In FIG. 2 there is illustrated the diaphragm ear valve 10 and ear fitting 12 with arrows indicating the path of normal sound eaves through the assembly.

The ear valve or sound transmitter 10 preferably includes a semi-circular inner bell housing 20 and semi-circular outer bell housing 22. The housings 20 and 22 are preferably formed of a relatively hard plastic. However, when the valve 10′ is utilized (FIG. 6) it is adapted to be positioned in the ear canal fitting 12′ and the need for the bell housing 20 is eliminated. Further, other means may be utilized to operatively associate the sound transmitter or valve 10 or 10′ with the ear fitting 12 or 12′.

Each of the housings 20 and 22 include flat mating surfaces 24 and 26 and the housings may be secured together along said surfaces by means of an epoxy or other adhesive.

While the housings 20 and 22 are preferably made of plastic for weight and ease of fabrication they can be manufactured of aluminum or other metal without departing from the spirit of the invention.

The inner bell housing 20 is formed with an annular groove 28 and a recess 29. Outer bell housing 22 has similar annular groove 30 and recess 32.

Figure 3:
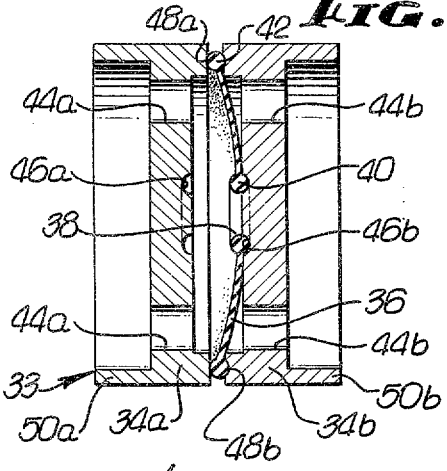
FIG. 3 is a cross-sectional view of the interior portion of the ear valve.

An inner valve assembly means generally designated 33 and particularly illustrated in FIG. 3, includes two identical annular diaphragm retainer means or rigid catcher plates 34a and 34b and a resilient annular diaphragm means generally designated 36.

Diaphragm 36 has a sound passage aperture or centrally located hole 38, an inner annular bead 40 formed around the periphery of hole 38, and projecting outwardly equidistant on each side of the diaphragm. Further, there is provided an outer annular bead 42 around the outer periphery of the diaphragm 36.

Catcher plates 34a and 34b each have a sound passage aperture axially aligned with the other, or a plurality of apertures 44a and 44b which are axially aligned near their outer edges. Also, plates 34a and 34b are provided with annular seats 46a and 46b around their central axes having a circumference equal to that of bead 40 on diaphragm 36. The plates 34a and 34b also include annular diaphragm retaining grooves 48a and 48b on the same sides as seats 46a and 46b. Around the peripheral edges of catcher plates 34a and 34b on the sides opposite grooves 46a and 46b and 48a and 48b are annular axially outwardly extending flanges 50a and 50b.

The circumference of diaphragm retaining grooves 48a and 48b is slightly larger than the circumference of outer bead 42 of diaphragm 36, so as to space the diaphragm therebetween when in an at rest position or generally fattened condition, see FIG. 2.

To assemble the inner valve assembly 33, the diaphragm 36 is positioned between the plates 34a and 34b with the bead 42 seated in grooves 48a and 48b so that the diaphragm 36 will be stretched radially outwardly and tensioned therebetween.

Flange 50a of catcher plate 34a seats within groove 30 of outer bell housing 22 and flange 50b of catcher plate 34b seats within groove 28 of inner bell housing 20 and each of the plates 34a and 34b are seated in the respective recesses 32 and 29. In this manner the inner valve assembly 33 is retained between the two bell housing portions.

An ear fitting adapter 52 is preferably screw fitted into an enlarged threaded portion 53 of axial bore 54 of inner bell housing 20. The adapter 52 has a plurality of annular flanges 56 around its periphery which fit in corresponding annular grooves 58 in the enlarged portion 60 of the axial bore 62 of ear fitting 12.

In normal operation when the incident overpressure of sound waves does not exceed a predetermined threshold, the ear valve operates as follows when inserted into a human ear as shown in FIG. 1 and previously described.

Sound waves, simulated by arrows in FIG. 2, pass through aperture 64 of outer bell housing 22 into bell chamber 66. The sound waves then pass through the several apertures 44a of catcher plate 34a through the space defined between the catcher plate 34a and diaphragm 36, through central opening 38 of diaphragm 36, through the space defined between the catcher plate 34b and diaphragm 36, and through apertures 44b of catcher plate 34b into bell chamber 68 of inner bell housing 20. The sound waves then pass through bore 54 and bore 62 into the ear.

However, when the incident overpressure of sound waves exceeds the predetermined threshold, the ear valve will close.

If the sound waves are percussive in nature they will pass through aperture 64 and bell chamber 66 of outer bell housing 20 and through apertures 44a of catcher plate 34a. Pressure buildup on the surface of diaphragm 36 will cause it to deflect inwardly in a catenary bow whereby a seal is created between *the cooperating valve surfaces defined by* bead 40 and seat 46b of catcher plate 34b, as shown in FIG. 3 thereby preventing passage of the overpressure wave into the ear.

If the overpressure sound wave is repercussive a partial vacuum will be created in bell chamber 66. The pressure differential between bell chamber 66 and bell chamber 68 will cause diaphragm 36 to deflect, again in the form of a catenary bow, toward the outer catcher plate 34a whereby a seal is created between bead 40 and seat 46a of said catcher plate to prevent a damaging increase in pressure on the ear drum.

Whether the overpressure wave is percussive or repercussive the diaphragm 36 will deflect from its normally at rest position, that is, on a perpendicular plane with said valve axis and spaced equidistant from said respective catcher plates 34a and 34b, in an annularly uniform catenary bow due to the uniform tensioning of the diaphragm 36 resulting from the slight variation in circumference between diaphragm bead 42 and diaphragm retaining grooves 48a and 48b. This tensioning and resiliency of diaphragm 36, plus its low inertia insure fast response to rapid fluctuations in the overpressure waves. Furthermore, the seating of bead 40 in seats 46a and 46b insures complete sealing between the diaphragm 36 and the catcher plates 34a and 34b, even under the stress of severe overpressure.

The valve shut-off threshold, the overpressure at which the diaphragm will deflect, can be predetermined and regulated by varying the size of diaphragm opening 38, the thickness of the diaphragm 36, the size of apertures 44a and 44b in the catcher plates 34a and 34b respectively, or the material from which the diaphragm is constructed.

Figure 5:
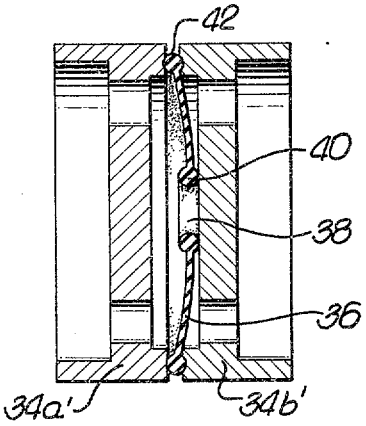
FIG. 5 is a cross sectional view of a modification of the interior portion of the ear valve.

The disclosure of FIG. 5 is substantially the same as the inner valve assembly means 33. However, the difference resides in the fact that the bead 40 surrounding the hole 38 of diaphragm 36 does not engage seats 46a and 46b but bears directly against the face of either plate 34a' or 34b'. In other words, the recessed seats are absent.

Figure 6:
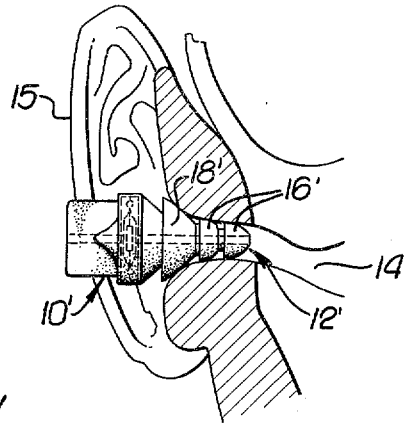
FIG. 6 is an environmental view of a modification of the diaphragm ear valve inserted in an ear canal fitting, and the entire assembly being fitted into the external auditory meatus of a human ear.

FIGS. 6 through 9 show a modification of the ear valve or sound transmitter 10' and the inner valve assembly 33'. In this particular modification, the inner valve assembly 33' is retained within the resilient ear canal fitting 12' remote from the flange 16' and 18'. Preferably, the fitting 12' includes an enclosed housing 70 which encompasses or includes an annular cavity 72. Projecting from the rear face 74 of the housing 70 is a generally solid finger gripping portion 76 to be grasped by the fingers so that the entire valve 10' may be seated in the ear such as seen in FIG. 6.

The housing 70 includes a bore 78 extending through the front wall 80 and a bore 82 in the rear wall 74 axially aligned with the bore 78. The bore 78 is *in* turn [in] aligned with bore 54' of the fitting 12'.

Figure 7:
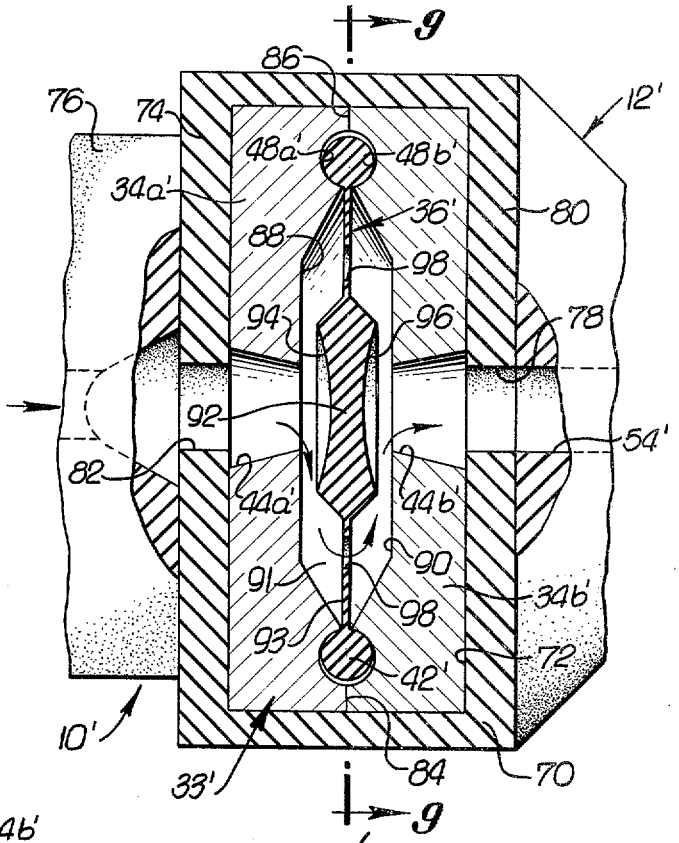
FIG. 7 is an enlarged cross sectional view of the modified assembly illustrated in FIG. 6.

Mounted within the cavity 72 of the housing 70 are a pair of rigid retainer means or catcher plates 34a' and 34b' of corresponding diameters and in parallel relationship one with the other. The catcher plates 34a' and 34b' are adapted to be butted together as best seen in FIG. 7. Each plate 34a' and 34b' includes a sound passage aperture 44a' and 44b' which are preferably tapered inwardly toward the diaphragm 36' so as to concentrate sound waves to the center of the diaphragm as best seen in FIG. 7. These apertures extend through each of the respective plates 34a' and 34b' and are in axial alignment as well as being axially aligned with the respective bores 82 and 78. Each of the plates 34a' and 34b' include inner faces 84 and 86 respectively, and in the central portion of the respective plates, annular interior recesses 88 and 90 are formed in the plates 34a' and 34b' respectively, creating a central chamber 91.

Further, each of the interior faces 84 and 86 are formed with opposed annular retaining grooves 48a' and 48b'.

The diaphragm 36' includes an annular peripheral bead 42' which is adapted to be gripped within the grooves 48a' and 48b' so as to maintain the diaphragm 36' in a vertical, at rest position stretching across the chamber 91. The diameter of the grooves 48a' and 48b' are slightly greater than the diameter of the diaphragm and bead so as to stretch the diaphragm when seated so that the position shown in FIG. 7 is achieved.

The diaphragm 36' differs from the diaphragm 36 in that the central portion 92 of the diaphragm 36' is enlarged in cross section having a thicker diameter than the normal flexible membrane portion 93 of the diaphragm 36'. Preferably, the central portion is formed with opposed concave surfaces or faces 94 and 96 which are adapted to close off the openings 44a' and 44b' such as illustrated in FIG. 8 when the overpressure wave moves into the assembly 10' in the direction of the arrows shown in FIG. 8.

In order to allow sound waves to pass from the exterior to the ear drum, the diaphragm preferably includes a pair of diametrically opposed sound passage apertures 98, out of axial alignment with the passages 44a' and 44b' so that the sound path is of sinuous configuration into the ear drum.

Figure 8:
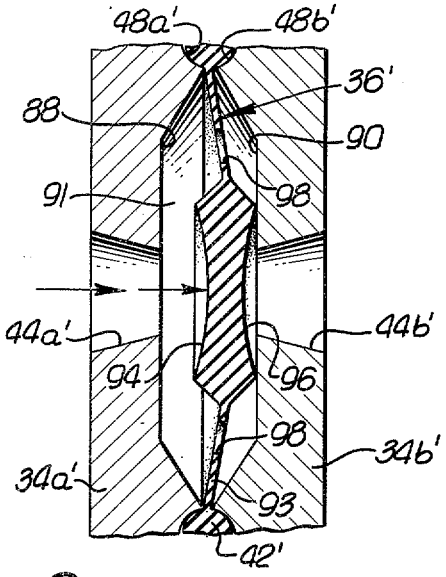
FIG. 8 is a cross sectional view of the modified assembly of FIG. 7 illustrating the valve closed.

As can be seen, when the *change in* sound *level* is either of an excessive percussive or repercussive nature, the diaphragm will be flexed and moved to the position such as seen in FIG. 8 or against the recess 88 in the case of repercussion, and the concave surfaces 94 and 96 will form a complete seal around the respective passages 44a' and 44b'. With the increase of pressure on the central portion 92 the concave surfaces or faces are further deformed toward a generally flat plane and greater sealing may be achieved.

Figure 9:
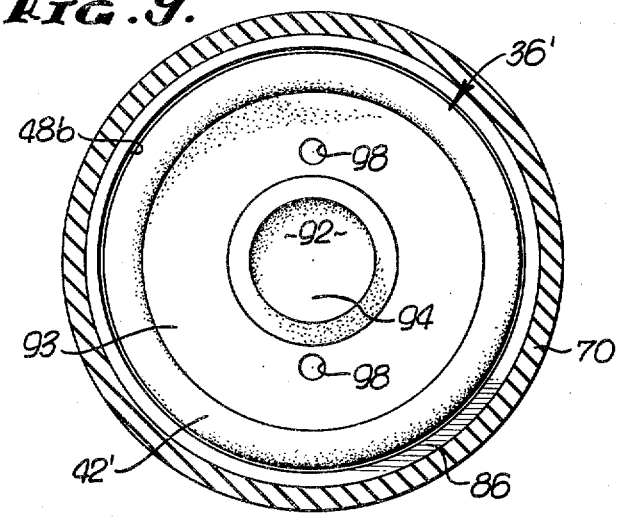
FIG. 9 is a view taken on line 9—9 of FIG. 7.
Figure 10:
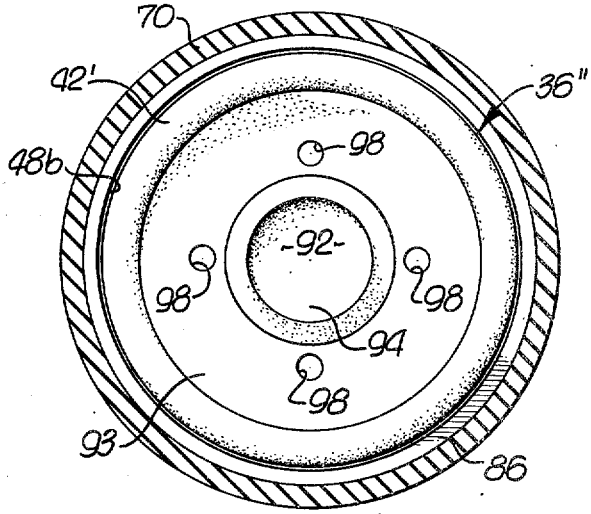
FIG. 10 is a modified form of the diaphragm illustrated in FIG. 9.

In FIG. 10 there is illustrated a diaphragm 36'' similar to that illustrated in FIG. 9 with the exception that there are a plurality of sound passageways 98 spaced peripherally around the diaphragm.

While the embodiment illustrated in FIGS. 6 through 9 shows the inner valve assembly 33 being integrally formed in the ear canal fitting 12' the invention is not limited to the particular configuration within the ear canal fitting 12' but can be utilized equally as well in the housing 20 configuration of FIGS. 1 through 5, which would then be affixed to an ear fitting, *or positioned in communication with an ear in any other equivalent manner.*

Although I have herein shown and described my invention in what I have conceived to be the most practical and preferred embodiment, it is recognized that departures may be made therefrom within the scope of my invention.

I claim:

1. In a sonic ear protector device wherein an ear canal fitting which includes a sound passage conveys sound waves reaching the passage, the combination with said fitting of a sound transmitter coupled with said fitting, the transmitter comprising parallel generally rigid plates spaced apart and a diaphragm between said plates locked around its periphery by said plates, a sound passage aperture through each plate in axial alignment, a sound passage aperture through the diaphragm axially offset from the sound passage apertures through the plates, the diaphragm being laterally spaced from the adjacent plates when reposing in generally flattened condition and the apertures in the plates and diaphragm in conjunction with the space on each side of the diaphragm affording a transmitter sound passage of sinuous configuration in communicating relationship with the sound passage of said fitting, the diaphragm including a relatively thin flexible membrane and a central annular sealing portion of relatively thicker cross section to provide a ring seal, whereby when said diaphragm is forced against either of said plates by the overpressure of sound waves said sealing portion will bear against the plate against which it is forced and create a seal closing off said transmitter sound passage.

2. The combination as defined in claim 1 wherein said sound passage apertures through said plates are axially aligned with said central annular sealing portion of said diaphragm and the diameter of said central annular sealing portion is greater than the diameter of said apertures in said plates.

3. The combination as defined in claim 1 wherein said central annular sealing portion of said diaphragm includes opposed sealing faces of concave configuration whereby said overpressure of sound waves will distort one of said faces to close off said transmitter sound passage.

4. The combination as defined in claim 1 wherein each of said sound passage apertures through said plates taper inwardly towards said diaphragm.

5. The combination as defined in claim 1 wherein said diaphragm includes an annular peripheral bead and said plates include opposed retainer grooves of a diameter slightly greater than the diameter of said diaphragm and said bead whereby when said bead is seated in said grooves said diaphragm will be radially stretched.

6. The combination as defined in claim 1 wherein said central annular sealing portion includes a sound passage aperture and an annular bead around said aperture, and said plates each include an annular seat wherein when said diaphragm is flexed said bead will engage one of said seats and provide a ring seal closing off said sound path.

*7. In a sonic ear protector device wherein an ear canal fitting which includes a sound passage conveys sound waves reaching the passage, the combination with said fitting of a sound transmitter coupled with said fitting, the transmitter comprising a pair of plates spaced apart and a diaphragm between said plates locked around its periphery, a sound passage aperture through each plate, a sound passage through the diaphragm axially offset from the sound passage apertures through the plates, the diaphragm being laterally spaced from the adjacent plates when reposing in generally flattened condition and the apertures in the plates and diaphragm in conjunction with the space on each side of the diaphragm affording a transmitter sound passage of sinuous configuration in communicating relationship with the sound passage of said fitting, the diaphragm including a relatively thin*

*flexible membrane and a central sealing portion of relatively thicker cross section to provide a seal, and a sealing surface on each plate on opposite sides of said sealing portion, said diaphragm being movable by sound wave pressure thereon to seat said sealing portion on either of said sealing surfaces to close said transmitter sound passage.*

*8. The invention defined in claim 7 wherein said sound passage apertures through said plates are axially aligned with said central sealing portion of said diaphragm and the diameter of said central sealing portion is greater than the diameter of said apertures in said plates.*

*9. The invention defined in claim 7 wherein said central sealing portion of said diaphragm includes opposed sealing faces of concave configuration.*

*10. The invention defined in claim 7 wherein each of said sound passage apertures through said plates taper inwardly towards said diaphragm.*

*11. The invention defined in claim 7 wherein said diaphragm includes an annular peripheral bead and said plates include opposed retainer grooves of a diameter slightly greater than the diameter of said diaphragm and said bead whereby when said bead is seated in said grooves said diaphragm will be radially stretched.*

*12. The invention defined in claim 7 wherein said central sealing portion includes a sound passage aperture and an annular bead around said aperture, and said sealing surfaces each include an annular seat for mating with said bead.*

*13. In an ear protector having an exterior housing, an outer sound passage, an inner sound passage, a sinuous central sound passage interconnecting said outer and inner sound passages and valve means for preventing transmission of excessive changes in sound level from the outer sound passage through the sinuous central sound passage to the inner sound passage, the improvement comprising:*

*a relatively flexible diaphragm with its periphery fixedly and sealably secured between the inner and outer sound passages;*

*first and second valve surfaces carried on opposite sides of said diaphragm near the center thereof;*

*first and second relatively fixed valve surfaces supported within said exterior housing and respectively spaced from opposite sides of said diaphragm adjacent the valve surfaces of said diaphragm;*

*an aperture forming a sound passage through the diaphragm;*

*said valve surfaces on the diaphragm surrounding said aperture;*

*the diaphragm valve surfaces being spaced from the adjacent fixed valve surfaces when the diaphragm is reposing in generally flattened condition;*

*the sinuous sound passage extending from the outer sound passage, between the opposed valve surfaces on one side of said diaphragm, through the aperture in the diaphragm, between the opposed valve surfaces on the other side of the diaphragm to the inner sound passage; and*

*the diaphragm being sufficiently flexible so that it will be deflected by a selected change in sound level from its flattened condition by a sufficient amount that one diaphragm valve surface will in cooperation with its facing fixed valve surface close the sinuous sound passage to protect the ear.*

*14. The ear protector of claim 13 wherein at least one of said inner and outer sound passages comprises a plurality of openings.*

*15. In an ear protector device for protecting the ear from damaging sound wave pressure levels and changes in pressure level, said ear protector device having a housing defining an outer sound passage for receiving sound waves and an inner sound passage through which received sound waves are communicated to the inner ear, the invention of improved sound valve means mounted in said housing longitudinally between said outer and inner sound passages to control and attenuate the flow of sound therebetween, said improved sound valve means comprising:*

*structure defining first and second spaced apart surfaces, at least one sound passage being defined in said structure to open on said first surface and to communicate with said outer and sound passage, at least one other sound passage being defined in said structure to open on said second surface and to communicate with said inner sound passage; and*

*diaphragm means mounted longitudinally between and spaced apart from said first and second surfaces for controlling the flow of sound therebetween, said diaphragm means having at least one aperture defined therein laterally offset from the points at which the sound passages open in said surfaces so that sound flowing from said outer to said inner sound passage follows a sinuous path through said valve means, said diaphragm means having a relatively thin membrane portion surrounding a thicker sealing portion, and a sealing surface on each of said first and second surfaces associated with said inner and outer sound passages, said sealing surfaces being in lateral alignment with said sealing portion, said sealing portion being movable by sound wave pressure on said diaphragm and being positioned for seating on one of said sealing surfaces to close said sinuous sound path.*

*16. The invention defined in claim 15, wherein said diaphragm means is mounted with its membrane portion radially stretched so that when sound waves are not being sensed it quickly returns to an at rest position.*

*17. The invention defined in claim 15, wherein:*

*said diaphragm means has only one of said apertures defined therein, said aperture being defined centrally in said diaphragm means;*

*said sealing portion is an annular bead around said aperture;*

*said sealing surfaces each have an annular seat defined therein for mating with said bead; and*

*the sound passages opening in said first and second surfaces open at points radially outside of said annular seats defined therein.*

*18. The invention defined in claim 15, wherein:*

*only one sound passage is defined to open in each of said first and second surfaces which opens centrally therein;*

*said sealing portion is centrally located on said diaphragm means and comprises opposed sealing faces of concave configuration which are larger than the sound passages defined to open centrally in said first and second surfaces; and*

*said aperture defined in said diaphragm means is positioned radially outside of said sealing portion.*

* * * * *